(12) United States Patent
Berberich et al.

(10) Patent No.: US 8,540,947 B2
(45) Date of Patent: Sep. 24, 2013

(54) METHOD FOR REDUCING ENTRAINMENT IN A STAINING DEVICE

(75) Inventors: Markus Berberich, Heidelberg (DE); Christian Wilke, Rimbach (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 324 days.

(21) Appl. No.: 13/178,618

(22) Filed: Jul. 8, 2011

(65) Prior Publication Data

US 2012/0009620 A1    Jan. 12, 2012

(30) Foreign Application Priority Data

Jul. 9, 2010   (DE) .......................... 10 2010 036 311

(51) Int. Cl.
*A61B 10/00*   (2006.01)

(52) U.S. Cl.
USPC ................. 422/536; 422/64; 422/65; 422/66; 422/67; 436/180

(58) Field of Classification Search
USPC .............................. 422/63–67, 536; 436/180
See application file for complete search history.

(56) References Cited

U.S. PATENT DOCUMENTS

| 5,573,727 | A | 11/1996 | Keefe |
| 6,017,495 | A | 1/2000 | Ljungmann |
| 6,635,225 | B1 | 10/2003 | Thiem et al. |
| 2010/0099133 | A1 | 4/2010 | Egle et al. |

FOREIGN PATENT DOCUMENTS

| GB | 1405940 | 9/1975 |
| WO | 93/23732 A1 | 11/1993 |

OTHER PUBLICATIONS

United Kingdom Intellectual Property Office, Combined Search and Examination Report in Application No. GB1111668.8, dated Oct. 25, 2011.

*Primary Examiner* — Jyoti Nagpaul
(74) *Attorney, Agent, or Firm* — Hodsgon Russ LLP

(57) ABSTRACT

During operation of a staining device (20) including a first container (22) filled with a first process medium (23) and a second container (24) filled with a second process medium (25), samples (26) to be stained are immersed in the first process medium (23). A speed representative of how fast the samples (26) are to be withdrawn from the first process medium (23) is determined according to the first process medium (23) and/or according to the samples (26). Subsequently, the samples (26) are withdrawn from the first process medium (23) at the determined speed.

14 Claims, 3 Drawing Sheets

| Step | Process Medium | Class | Speed | Entrainment |
|---|---|---|---|---|
| 1 | Alcohol 100% | Alcohol | 14,55 mm/s | 2,4 g |
| 2 | Alcohol 95% | Alcohol | 14,55 mm/s | 2,4 g |
| 3 | Rinse | Water | 26,67 mm/s | 2,5 g |
| 4 | Distilled Water | Water | 26,67 mm/s | 2,5 g |
| 5 | Alcohol 100% | Alcohol | 14,55 mm/s | 2,4 g |

METHOD FOR REDUCING ENTRAINMENT IN A STAINING DEVICE

CROSS REFERENCE TO RELATED APPLICATIONS

This application claims priority of German patent application number 10 2010 036 311.1 filed Jul. 9, 2010, the entire disclosure of which is incorporated by reference herein.

FIELD OF THE INVENTION

The present invention relates to a method for operating a staining device including a first container filled with a first process medium and a second container filled with a second process medium. The samples to be stained are immersed in the process medium in the first container. After a predetermined residence time has elapsed, the samples are withdrawn from the first process medium and located above the second container.

BACKGROUND OF THE INVENTION

Samples, in particular tissue samples to be examined using a microscope, are routinely stained using staining devices, so that structures of the samples can be better seen in the microscopic image than in the case of unstained samples. For sample staining, a staining device includes two or more containers in which identical, similar or different process media are stored. The samples to be stained are immersed in the containers, where they remain for residence times which are dependent on the process step, the process medium, and on the sample to be stained. Once the predetermined residence time has elapsed, the samples are withdrawn from the container. Depending on the staining method and/or the sample, the samples are successively immersed in a plurality of containers filled with process media.

When the samples are rapidly withdrawn from a first container filled with a first process medium, small amounts of the first process medium remain adhered to the samples, in particular tissue samples, to slides carrying the tissue samples and/or to a sample basket for carrying the samples, and/or drip off from the samples once they are withdrawn from the process medium. When the samples are then rapidly moved over a second container which follows the first container and is filled with a second process medium, then the first process medium of the first container drips into the second process medium of the second container. When the samples are immersed in the second process medium in the second container, then all of the first process medium adhering to the samples gets into the second process medium. In this manner, the first process medium is entrained, causing the amount of the first process medium in the first container and the quality of the second process medium in the second container to be reduced. This has a negative effect on the quality of the staining process. In particular, the stained samples may have less color contrast and/or a lower color content. If, in contrast, the samples are slowly withdrawn from the first process medium and left suspended above the first container for a long time after withdrawal, then this reduces entrainment, but has a negative effect on the duration of the staining process in that it increases the same.

From the document DE 196 81 642 C2, a staining device for staining tissue samples on slides is known, which comprises a plurality of containers with liquids, said containers being arranged in a stepped manner relative to one another. Baskets in which the slides are accommodated are immersed in the containers for staining. Upon removal via a transport mechanism, the baskets are removed such that they brush against an edge of the respective container so as to wipe off liquid adhering to the basket.

From the document U.S. Pat. No. 5,573,727 A, a staining device is known which comprises a plurality of containers with liquids in which the racks with the samples to be stained are immersed. Here, several racks are simultaneously handled in the device, the transport of the racks taking place according to a fixed schedule.

SUMMARY OF THE INVENTION

It is an object of the present invention to provide a method for operating a staining device, which method will contribute in a simple manner to keeping the duration of the staining process short, to keeping the cost of the process low and/or to ensuring high-quality staining of the samples.

In a first aspect of the present invention, a speed at which the samples are to be withdrawn from the first process medium is determined according to the first process medium and/or according to the samples. Subsequently, the samples are withdrawn from the first process medium at the determined speed. The aforesaid speed may be an average speed or a speed at which the samples are mainly moved.

This makes use of the fact that the amount of the first process medium that remains adhered to the samples, in particular to the tissue samples and slides, or to sample baskets is directly dependent on the speed at which the samples are withdrawn from the process medium. In other words, a relatively large amount of process medium remains adhered to the samples if they are rapidly withdrawn, while a relatively small amount of process medium remains adhered to the samples if they are slowly withdrawn from the first process medium. Moreover, the adherence of the process medium to the samples is dependent on the type of process medium and on the type of the samples and especially the surface thereof. In this context, the samples include not only the actual tissue samples to be examined, but may also include the slides carrying the tissue samples and/or sample cassettes in which the tissue samples or slides are placed. Determining the speed at which to withdraw the samples may contribute to keeping the entrainment of process media to particularly low levels, while still allowing the staining process to be performed in a relatively short period of time. This contributes to keeping the process media relatively pure over a long period of time, so that they need to be replaced less frequently, which helps keep the cost of the process low and the staining quality high.

In a second aspect of the present invention, a period of time to elapse until the samples have been withdrawn from the first process medium and moved over the second container is determined according to the first process medium and/or according to the samples. Subsequently, the samples are withdrawn from the first container in such a manner that they are located above the second container after the determined period of time has elapsed. The samples are considered to be located above the second container as soon as the process medium can drip from the samples into the second container. The aforesaid period of time may be the period from the beginning of the withdrawal movement to the arrival at the position above the second container, or the period from the point of exit from the first process medium to the arrival at the position above the second container.

This makes use of the fact that different process media need different periods of time until they have dripped off from samples of the same type, and that identical process media drip off from different types of samples at different rates.

Thus, the drip-off rate depends on both the process medium and the sample. The determination of the period of time for withdrawing the samples from the first container and locating the samples above the second container can contribute to keeping the entrainment of process media to particularly low levels, while still allowing the staining process to be performed in a relatively short period of time. This contributes to keeping the process media relatively pure over a long period of time, which helps keep the staining quality high and extend the period of usefulness of the process media.

In an advantageous embodiment, the speed and the period of time are determined. The samples are then withdrawn from the first container at the determined speed and located above the second container within the determined period of time. For example, the samples are withdrawn from the first process medium at the determined speed and then moved toward the second container within the determined period of time. This contributes particularly effectively to low entrainment levels and high process rates because the samples are withdrawn from the first process medium at optimum speed and, in addition, are allowed to drain to a sufficient degree.

The speed and/or the period of time may be determined, for example, by means of an assignment rule. The assignment rule includes, for example, a table in which each process medium, each sample and/or each combination of a process medium and a sample are assigned at least one speed and/or a period of time. In other words, a table, in which each process medium used, or each sample used, or each combination of a process medium and a sample is assigned a speed and/or a period of time, is stored on a storage medium of the staining device. The speeds and/or periods of time of the assignment rule may, for example, be determined empirically. Alternatively, or in addition, the speeds and/or periods of time are determined according to a viscosity of the process media and/or according to a material of the samples.

In an alternative embodiment, the process media and/or the samples are divided into classes, and each class of process media or samples is assigned a speed and/or a period of time.

Further, for given samples and given process media, the speed and/or the period of time are determined according to a permitted entrainment level and/or according to a process duration to be observed. This enables optimal adjustment of the staining quality and process duration. In other words, a user may specify a maximum duration for the staining process and/or a maximum acceptable level of entrainment, and the speed and/or period of time are then determined according to the maximum duration of the staining process or the maximum acceptable level of entrainment.

BRIEF DESCRIPTION OF THE DRAWINGS

Exemplary embodiments of the present invention are described in more detail below with reference to the schematic drawings, in which.

Elements having the same design or function are identified by the same reference numerals throughout the figures.

DETAILED DESCRIPTION OF THE INVENTION

Figure 1:
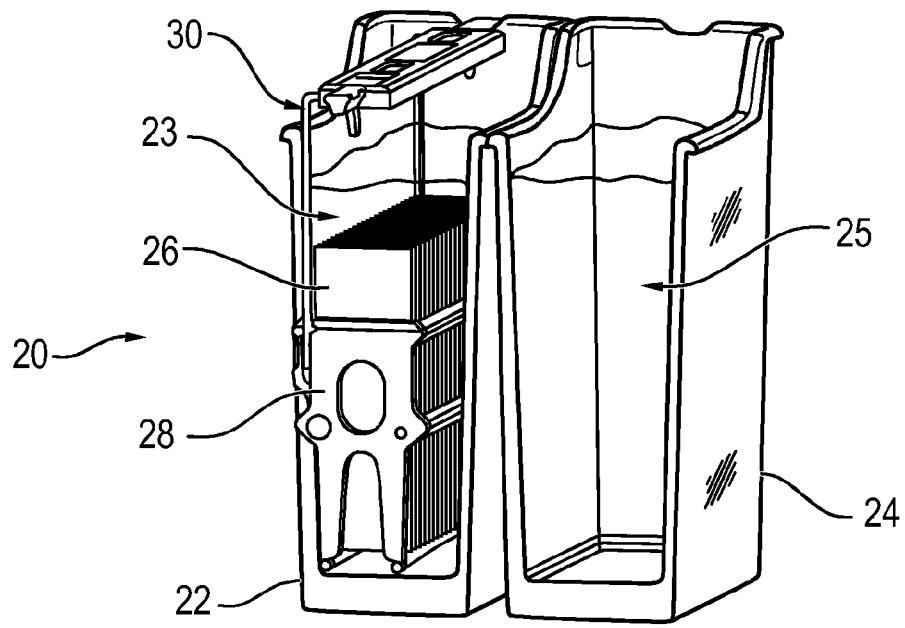
FIG. 1 is a cross-sectional view showing a staining device with samples in a first position.

FIG. 1 shows a staining device 20 for staining samples 26, in particular tissue samples. Staining device 20 includes a first container 22 and a second container 24. First container 22 is filled with a first process medium 23. Second container 24 is filled with a second process medium 25. Samples 26 are disposed in a sample basket 28. Sample basket 28 is coupled to a lifting device 30. Samples 26 may be placed directly into sample basket 28. Alternatively, samples 26 may be arranged in sample cassettes, which are then placed into the sample basket. The process medium used may be, for example, alcohol in different concentrations, xylene, water, distilled water, hematoxylin or eosin Y. Samples 26 include, for example, the tissue samples, an embedding medium, such as paraffin, in which the tissue samples are embedded, and/or slides carrying the samples.

Samples 26 are immersed in process media 23, 25 for cleaning and/or staining. Samples 26 remain in process media 23, 25 for residence times which are dependent on samples 26 and process media 23, 25. The predetermined residence times are stored, for example, on a storage medium of staining device 20. Once the predetermined residence time has elapsed, samples 26 are withdrawn from process media 23, 25.

Figure 2:
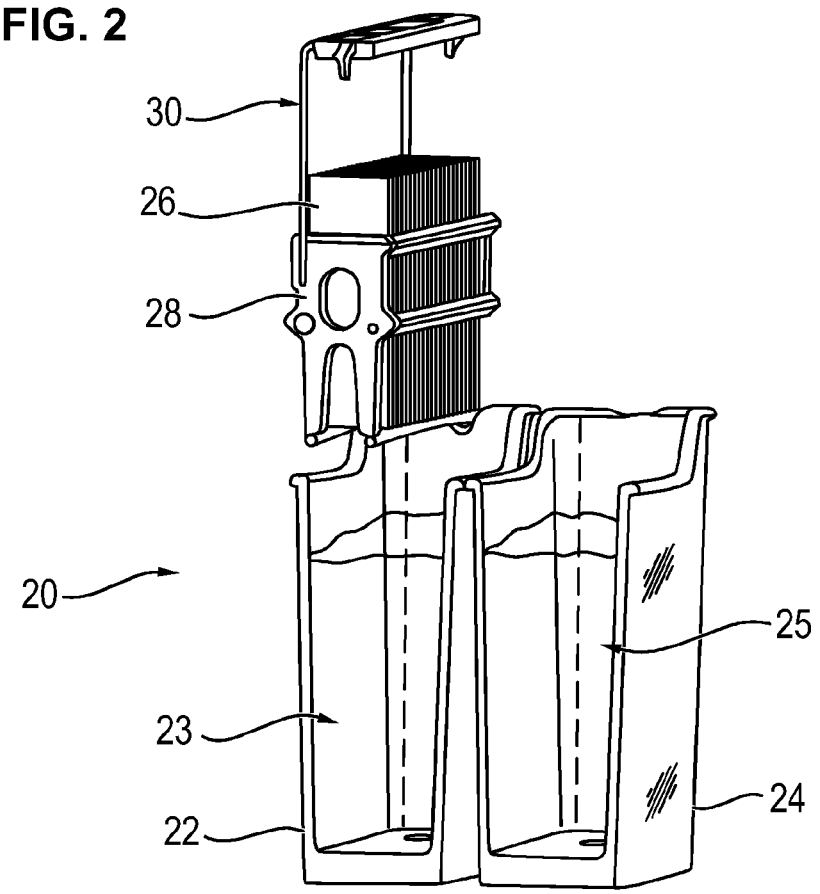
FIG. 2 is a cross-sectional view showing the staining device with samples in a second position.

FIG. 2 shows staining device 20 with sample basket 28 in the withdrawn position. In the withdrawn position, first process medium 23 drips into first container 22. When now sample basket 28 is moved over second container 24, then the first process medium drips into second process medium 25 in second container 24 and is entrained in this manner. When sample basket 28 is immersed in second container 24, then the amount of first process medium 23 that adheres to samples 26 is introduced into second process medium 25 and is entrained in this manner.

The movement of samples 26 from first container 22 over second container 24 is divided into at least two phases. In the first phase, samples 26 are still located within first process medium 23, but are being withdrawn. In the second phase, samples 26 have already been withdrawn from first process medium 23, but have not yet been moved far enough above second container 24 that first process medium 23 would be able to drip into second process medium 25. The entrainment is substantially influenced by two factors. The first factor is the speed at which samples 26 are withdrawn from first process medium 23 during the first phase. The faster samples 26 are withdrawn, the greater is the entrainment. The slower samples 26 are withdrawn, the lower is the entrainment. The second factor is the period of time that elapses until samples 26 are located above second container 24 in such a way that first process medium 23 may drip into second process medium 25. This period of time may begin at the moment when the movement of samples 26 out of first process medium 23 begins, or at the moment when samples 26 have been completely moved out of first process medium 23. In other words, the speed relates exclusively to the first phase, while the period of time relates to the second phase or to both phases. Thus, the second period of time includes at least a drip-off time above first container 22 and may additionally include the time needed for withdrawal from first process medium 23.

In order to keep entrainment to a minimum while still being able to achieve a short process duration, preferably, the speed is determined at which samples 26 are to be withdrawn from first process medium 23. Alternatively, or in addition, it is possible to determine the period of time to elapse until samples 26 have been withdrawn from the first container 22 and located above second container 24. The speed and the period of time are preferably determined empirically and stored, for example, in an assignment rule on the storage medium. In the empirical determination of the speed and the period of time, respectively, a maximum acceptable duration of the staining process and/or a maximum acceptable level of entrainment may be input as boundary conditions. A relatively short process duration is associated with a relatively high level of entrainment, while a relatively low level of entrainment is associated with a relatively long process duration.

Figures 3, 4:
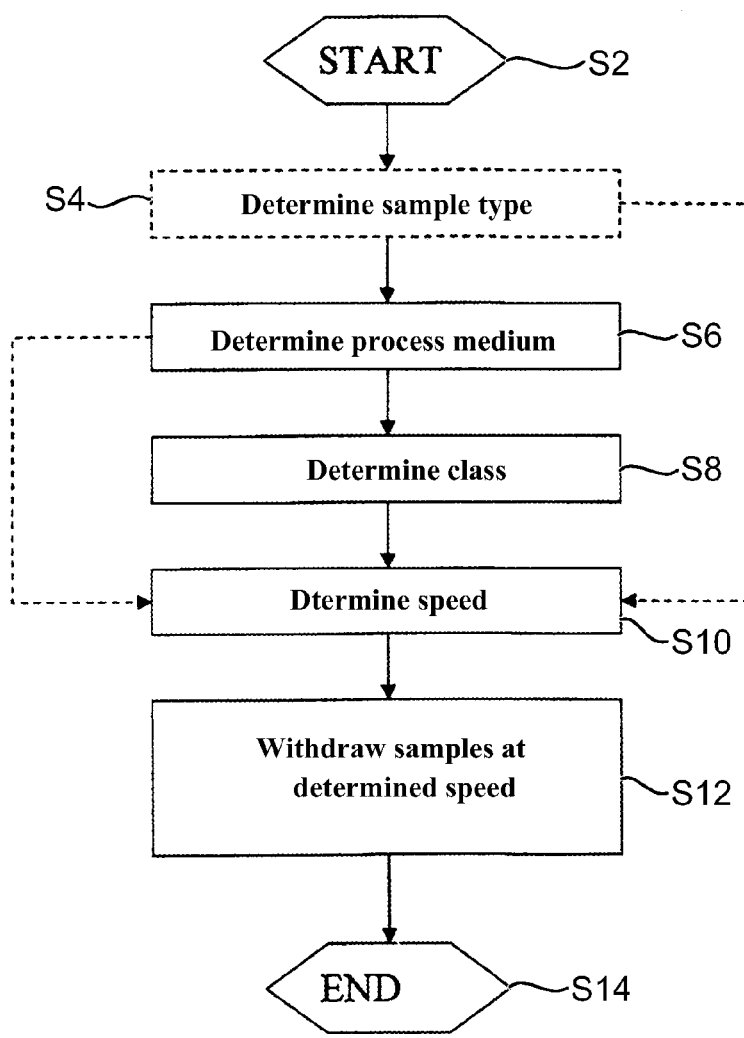
FIG. 3 shows an assignment rule.
FIG. 4 is a flow chart of a first program for operating the staining device.

FIG. 3 shows an assignment rule which illustrates the speeds at which samples 26 are to be withdrawn from different process media 23, 25. The assignment rule includes a table having 5 columns. The first column enumerates the steps for staining samples 26. The second column lists process media 23, 25, in particular 100% alcohol, 95% alcohol, rinse, and distilled water. Process media 23, 25 are divided into two classes, specifically into alcohols and water. According to the assignment rule shown, samples 26 are to be withdrawn from the alcohols at a speed of 14.55 mm/s, which results in an entrainment of 2.4 g per step. In contrast, samples 26 are to be withdrawn from the water at a speed of 26.67 mm/s, which results in an entrainment of 2.5 g per step.

If a higher level of entrainment is acceptable for specific samples 26, then the speed may be increased, thereby shortening the staining process. Similarly, if the duration of the staining process is of minor importance, the speed may be reduced, so that the level of entrainment is reduced, process media remain pure over a longer period of operation, and samples 26 are stained in a high-quality manner. For example, the maximum acceptable duration of the staining process and/or the maximum acceptable level of entrainment may be input by a user at the beginning of the staining process, and the speed and the period of time are then determined according to the maximum acceptable duration of the staining process and/or the maximum acceptable level of entrainment, respectively. To this end, different assignment rules may be stored on the storage medium of staining device 20, for example, for different maximum acceptable process durations and/or maximum acceptable entrainment levels.

FIG. 4 shows a flow chart of a first program for operating the staining device, which may be stored, for example, on the storage medium of staining device 20. The first program is preferably started in a step S2, for example, when samples 26 are immersed into first container 22.

In a step S4, a sample type may be determined for samples 26 to be stained. The sample type may be determined, for example, by a query and a corresponding input from a user of the staining device. Alternatively, samples 6 may be provided with a code, such as a bar code, so that the sample type can be detected by a sensor device.

If only the sample type is relevant, for example when different containers 22, 24 contain a plurality of process media 23, 25 of the same type, then the method may proceed directly to a step S10, in which the speed at which samples 26 are to be withdrawn is determined according to the sample type. Otherwise, the method is continued in a step S6. If only the type of first process medium 23 is not relevant, then step S4 may be skipped, and the program may proceed directly to step S6.

In a step S6, first process medium 23, in particular the type of first process medium 23, is determined. As above, first process medium 23 may be queried from a user. Alternatively, staining device 20 has a sensor device capable of determining the type of first process medium 23 in first container 22. If only the type of first process medium 23 is relevant, for example when routinely using samples 26 of the same type, then the method may proceed directly to step S10. Alternatively, the method is continued in a step S8. Moreover, if the type of type of first process medium 23 and the type of samples 26 are relevant, it is possible to initially execute steps S4 and S6 and then proceed directly to step S10.

In a step S8, a class is determined to which sample 26 and/or process medium 23, 25 belong.

In a step S10, the speed at which to withdraw samples 26 may then be determined according to the determined sample type and/or the determined first process medium 23.

In a step S12, samples 26 are withdrawn from first process medium 23 at the determined speed and/or located above second container 24 within the determined period of time after the predetermined residence time in first process medium 23 has elapsed.

In a step S14, the method may be terminated. Preferably, however, the method is continuously executed during the operation of staining device 20.

Besides the speed at which samples 26 are withdrawn from first process medium 23, the entrainment is also affected by the period of time that elapses until samples 26 are suspended above second container 24 and first process medium 23 may drip into second process medium 25. Therefore, a second program stored on the storage medium may be executed as an alternative or in addition to the first program.

Figure 5:
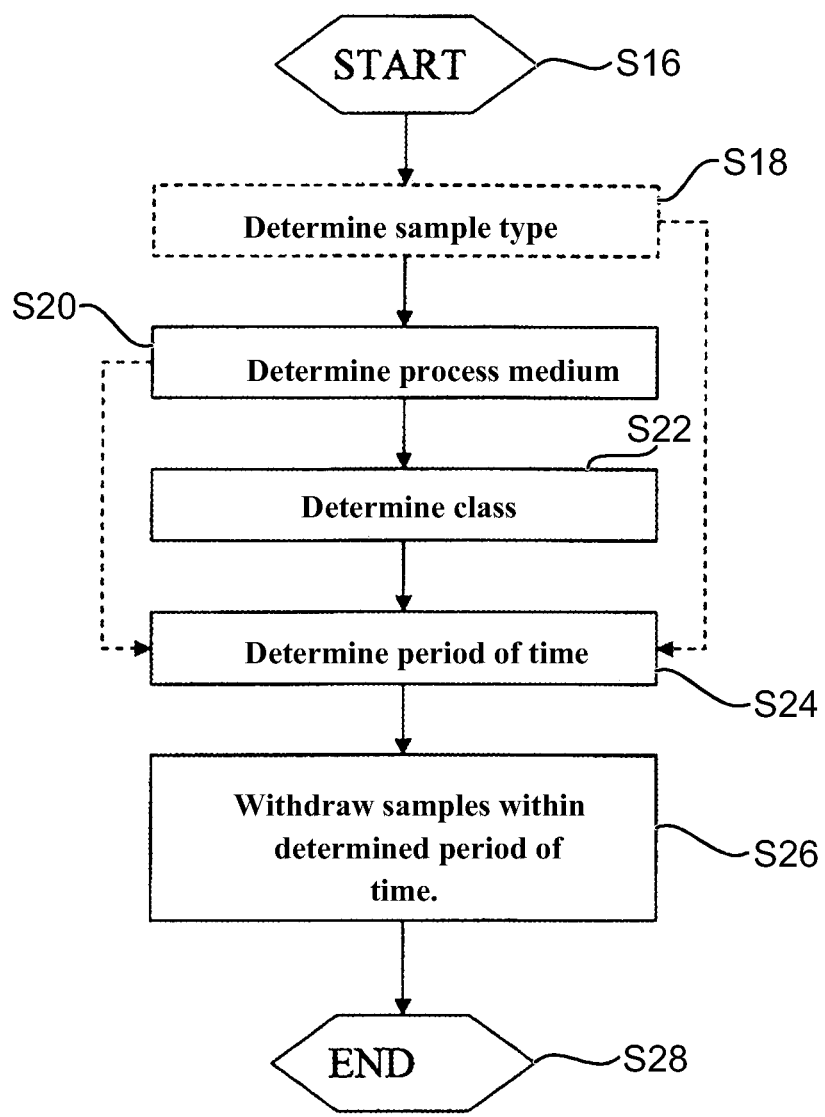
FIG. 5 is a flow chart of a second program for operating the staining device.

FIG. 5 shows a flow chart of the second program for operating staining device 20. This second program is preferably started in a step S16, for example, when samples 26 are immersed into first container 22.

In a step S18, the type of samples 26 to be stained may be determined, for example, as in step S4 of the first program. If only the sample type is relevant, for example when different containers 22, 24 contain a plurality of process media 23, 25 of the same type, then the method may proceed directly to a step S24, in which the period of time for withdrawing samples 26 may then be determined according to the determined sample type and/or the determined first process medium 23. Otherwise, the method is continued in a step S20. If only the type of first process medium 23 is relevant, then step S18 may be skipped, and the program may proceed directly to step S20.

In step S20, first process medium 23, in particular the type of first process medium 23, is determined, for example, as in step S6 of the first program. If only the sample type is relevant, then step S20 may be skipped.

In a step S22, a class is determined to which sample 26 and/or process medium 23, belong. Alternatively, step S24 may be executed directly after step S20.

In step S24, the period of time for withdrawing samples 26 may then be determined according to the determined sample type and/or the determined first process medium 23.

In a step S26, samples 26 are moved above second container 24 within the determined period of time after the predetermined residence time in first process medium 23 has elapsed.

In a step S28, the method may be terminated. Preferably, however, the method is continuously executed during the operation of staining device 20.

The present invention is not limited to the exemplary embodiments described herein. For example, staining device 20 may include far more than two containers 22, 24 containing a far greater number of different process media 23, 25. Further, the method for operating staining device 20 may be executed differently in terms of time. In particular, at the very beginning when samples 26 are introduced into staining device 20, the sample type may be entered into staining device 20 and/or the type of process medium 23, 25 may already be known. In that case, the method, in each step, only queries the speed at which samples 26 are to be withdrawn from the respective container 22, 24 or within which period of time samples 26 are to be moved above second container 24.

LIST OF REFERENCE NUMERALS 20 staining device
22 first container
23 first process medium
24 second container
25 second process medium
26 samples
28 sample basket
30 lifting device
S2-S28 steps two through twenty-eight

What is claimed is:

1. A method for operating a staining device (20), comprising the steps of:
providing a first container (22) filled with a first process medium (23) and at least one second container (24) filled with a second process medium (25);
immersing samples (26) to be stained in the first process medium (23);
determining a speed representative of how fast the samples (26) are to be withdrawn from the first process medium (23) according to the first process medium (23) and/or according to the samples (26), wherein the determined speed is determined using an assignment rule in which each process medium (23), each sample (26), and/or each combination of process medium (23) and sample (26) is assigned at least one speed; and
withdrawing the samples (26) from the first process medium (23) at the determined speed.

2. The method of claim 1, further comprising the steps of determining a period of time to elapse before the samples (26) are located over the second container (24), wherein the period of time is determined using a further assignment rule in which each process medium (23), each sample (26) and/or each combination of process medium (23) and sample (26) is assigned at least one period of time according to the first process medium (23) and/or according to the samples (26); and
locating the withdrawn samples (26) above the second container (24) after the determined period of time has elapsed.

3. The method of claim 1, wherein the determined speed is determined according to a viscosity of the first process medium (23).

4. The method of claim 1, wherein the determined speed is determined according to a material contained in the samples (26).

5. The method of claim 1, wherein the process media (23, 25) and/or the samples (26) are divided into classes; and the determined speed is determined according to the classes.

6. The method of claim 1, wherein, for given samples (26) and given process media (23, 25), the determined speed is determined according to a permitted entrainment level and/or according to a process duration to be observed.

7. The method of claim 1, wherein, for given samples (26) and given process media (23, 25), the determined speed is determined according to a permitted entrainment level.

8. A method for operating a staining device (20) including at least one first container (22) filled with a first process medium (23) and a second container (24) filled with a second process medium (25), comprising the steps of:
immersing samples (26) to be stained in the first process medium (23);
withdrawing the samples (26) from the first process medium (23);
determining a period of time to elapse before the samples (26) are located over the second container (24), wherein the period of time is determined using an assignment rule in which each process medium (23), each sample (26) and/or each combination of process medium (23) and sample (26) is assigned at least one period of time according to the first process medium (23) and/or according to the samples (26); and
locating the withdrawn samples (26) above the second container (24) after the determined period of time has elapsed.

9. The method of claim 8, wherein the period of time includes time elapsed while the samples are withdrawn from the first process medium.

10. The method of claim 8, wherein the period of time is determined according to a viscosity of the first process medium (23).

11. The method of claim 8, wherein the period of time is determined according to a material contained in the samples (26).

12. The method of claim 8, wherein the process media (23, 25) and/or the samples (26) are divided into classes; and
the period of time is determined according to the classes.

13. The method of claim 8, wherein, for given samples (26) and given process media (23, 25), the period of time is determined according to a permitted entrainment level and/or according to a process duration to be observed.

14. The method of claim 8, wherein, for given samples (26) and given process media (23, 25), the period of time is determined according to a permitted entrainment level.

* * * * *